United States Patent [19]

Griggs et al.

[11] Patent Number: 4,520,265
[45] Date of Patent: May 28, 1985

[54] METHOD AND APPARATUS FOR ACCURATE REMOTE MONITORING OF GASES

[75] Inventors: Michael Griggs, San Diego; Laurence L. Action, La Jolla; Gordon D. Hall, San Diego, all of Calif.

[73] Assignee: Southern California Gas Co., Los Angeles, Calif.

[21] Appl. No.: 529,576

[22] Filed: Sep. 6, 1983

[51] Int. Cl.³ ............................................... G01J 1/00
[52] U.S. Cl. .................................... 250/338; 250/339; 250/343
[58] Field of Search ............... 250/343, 342, 339, 345, 250/344, 338; 356/437

[56] References Cited
U.S. PATENT DOCUMENTS
3,976,884  8/1976  Acton et al. .......................... 250/343
4,157,470  6/1979  Kotaka et al. ........................ 250/345

OTHER PUBLICATIONS

Herget, W. et al., "Infrared Gas-Filter Correlation Instru. for In Situ Means of Gaseous Pollutant Con.", Applied Optics, vol. 15, No. 5, (1976), p. 1222.

Primary Examiner—Alfred E. Smith
Assistant Examiner—Richard E. Hanig
Attorney, Agent, or Firm—Bruce L. Birchard

[57] ABSTRACT

Apparatus is provided which permits highly accurate remote measurement of methane gas concentrations even in daylight through the use of an extremely narrow spectral filter centered on the Q-branch of the methane absorption band at 3.3 microns and through the use of cooperating comparison channels with digital processing for real time correction of data to compensate for surface temperature, atmospheric temperature and atmospheric water absorption factors.

14 Claims, 4 Drawing Figures

METHOD AND APPARATUS FOR ACCURATE REMOTE MONITORING OF GASES

BACKGROUND OF THE INVENTION

1. Field of the Invention

This invention relates to gas monitoring apparatus and more particularly to infrared remote gas-filter correlation (RGFC) sensors.

2. Prior Art

Reference is made to U.S. Pat. No. 3,976,884 issued Aug. 24, 1976 to Acton, et al and entitled "Method for Remote Monitoring of Gaseous Products" the subject matter of which relates to but does not anticipate the present invention. Further reference is made to a paper entitled "A Gas Filter Correlation Instrument for Atmospheric Trace Constituent Monitoring" authored by W. D. Hesketh, H. G. Reichle, W. A. Messey, T. V. Ward and H. H. Zwick and presented at the Fifth Annual Remote Sensing of Earth Resources Conference, Tullahoma, Tenn., Mar., 1976 which discloses related material but does not anticipate this invention.

It is necessary for health, safety and sound economic reasons that the loss of gaseous fuels, such as methane, from buildings, city-wide distribution lines and long-distance pipelines be detected promptly and accurately. Infrared remote gas filter correlation (RGFC), broadly, is not new.

The RGFC technique has been used in various forms for measuring from ground-based, aircraft, and space platforms trace gases in the atmosphere. These previous instruments used analog electronic signal processing and made certain assumptions about the effects of the background and atmospheric radiances in order to produce a readout of the gas concentration. In this invention digital electronics and microprocessors are used so that more accurate corrections for the background and atmospheric radiances can be made in real time.

For certain gases previous apparatus has been sensitive to reflected sunlight and to thermal radiation (i.e., radiation in the 2-4 micron region, approximately). This has been true for methane being detected at 3.3 microns. Interpretation of the daylight produced signal is very complicated and has restricted the use of the apparatus to the nighttime.

Therefore, it is one object of this invention to overcome the various problems encountered in the use of previous RGFC apparatus.

It is another object of this invention to provide RGFC apparatus which is blind to reflected solar radiation.

It is a still further object of this invention to provide a gas monitoring method and apparatus which is free of restriction to nighttime use and rapidly provides accurate results.

SUMMARY OF THE INVENTION

Stated succinctly, in this invention the effect of reflected sunlight is made negligible by using an extremely narrow spectral filter centered on the Q-branch of the methane absorption band at 3.3 μm. The transmittance in this bandpass of the ambient methane (approximately 1.8 ppm) and water vapor always present in the atmosphere is very low so that the amount of solar radiation at that wavelength reaching the earth's surface is very small, and makes the apparatus of this invention "quasi-solar-blind." Further, with this invention, by utilizing digital techniques and adequate numbers of comparison channels, real time corrections can be made in the output data for surface temperature, atmospheric temperature and atmospheric water absorption factors.

BRIEF DESCRIPTION OF THE DRAWINGS

The features of the present invention which are believed to be novel are set forth in the appended claims. The present invention, both as to its organization and manner of operation, together with further objects and advantages therof, may best be understood by reference to the following description, taken in conjunction with the accompanying drawings, in which:

DETAILED DESCRIPTION OF THE PREFERRED EMBODIMENT

Figure 1A:
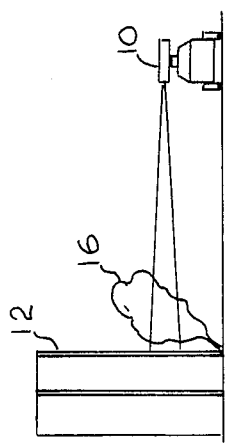
FIG. 1a is a diagrammatic representation of one type of environment in which the present invention can be used.
Figure 1B:
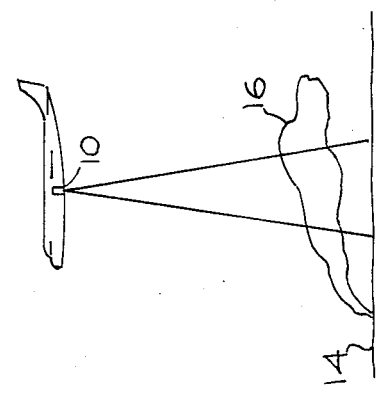
FIG. 1b is a diagrammatic representation of a second type of environment in which this invention can be used.

In detecting gas leaks, as is illustrated for two cases in FIGS. 1a and 1b, respectively, the RGFC sensor 10 is receiving infrared radiation from the background surface (such as building 12 or earth's surface 14), from the atmosphere, from the leaking gas cloud 16, and from sunlight reflected off of the background surface, either building 12 in FIG. 1a or the earth's surface 14 in FIG. 1b. For an aircraft at low altitudes ($\leq 1000$ m), or for a short horizontal path from a truck, we can assume a homogeneous single-slab atmospheric model, so that the radiance ($E_T$) incident on the sensor 10 is given by:

$$E_T = \frac{E_S \cos \theta\, R}{\pi} \tau + \epsilon E(T_S)\tau + E(T_A)(1 - \tau) \tag{1}$$

wherein
- $E_S$ is the solar irradiance at the ground
- $\theta$ is the solar zenith angle
- $R$ is the surface reflectivity
- $\tau$ is the atmospheric transmissivity (surface to sensor 10)
- $\epsilon$ is the surface emissivity ($=1-R$)
- $E(T)$ is the black body radiance at temperature T
- $T_S$ is the surface temperature and
- $T_A$ is the atmospheric temperature The total transmissivity ($\tau$) is given by the product of the species transmissivities in that bandpass $$\tau = \tau_1 \tau_2 \tau_3 \tag{2}$$

For these calculations it is assumed that only methane and water vapor will absorb energy in the GFC passband. Aerosol attenuation will be negligible for the path lengths of concern here and it is assumed that other hydrocarbons will be of a negligible concentration.

The parameters in equation (1) are functions of wavelength, but for the narrow spectral bandpass of this apparatus, as described in connection with FIG. 2, band-averaged values of these parameters may be used.

The band-average value of the gaseous transmissivity is given by $$\tau = \exp\left[\frac{\bar{k}pcl}{(1 + \bar{k}cl/4a_o)^{\frac{1}{2}}}\right] \quad (3)$$

where
  $\bar{k}$ is the band-average absorption coefficient
  p is the total pressure
  c is the species concentration
  l is the path length over which the species is measured, and
  $a_o$ is the ratio of the line half-width to line spacing at 1 atmosphere pressure. NOTE: For the temperature and pressure ranges encountered and under the conditions of typical use the temperature dependence of the pressure term in Eq. 3 is negligible and can be ignored.

Using values of k and $a_o$ derived from previous work described in a paper by C. B. Ludwig, M. Griggs, W. Malkmus and E. R. Bartle, entitled "Air Pollution Measurements from Satellites," NASA CR-2324, Nov. 1973, it is found that for the 3000–3030 cm$^{-1}$ band utilized in this invention, the ambient methane and water vapor significantly attenuate the incoming solar radiation so that the first term in equation (1) is always less than 10$^{-2}$ times the remaining terms and can be neglected, i.e., the GFC sensor 10 according to this invention is "quasi-solar-blind." This is an important conclusion since it means that the sensor 10 will not be affected by varying solar illumination, and will give the same output day and night (for the same atmospheric and surface conditions).

The signal change (SC) is given by the difference in $E_T$ for an atmosphere with and without methane:

$$SC = [\epsilon E(T_S)\tau_W + E(T_A)(1 - \tau_W)] - [\epsilon E(T_S)\tau_W\tau_M + E(T_A)(1 - \tau_W\tau_M)] \quad (4)$$

where
  $\tau_W$ is the water vapor transmissivity and
  $\tau_M$ is the methane transmissivity.
Equation (4) may be rearranged to give $$SC = [\epsilon E(T_S) - E(T_A)](1 - \tau_M)\tau_W \quad (5)$$

Of course the unknown we are attempting to quantify is methane concentration which can be determined directly from $\tau_M$. It is seen in equation (5), that the calculated SC is very sensitive to surface temperature (and atmospheric temperature) changes. Previous GFC sensors have minimized this sensitivity by ratioing SC to the signal through the vacuum cell of the GFC. However, the vacuum cell signal measures $[\epsilon E(T_S) - E(T_A)]\tau_M\tau_W + E(T_A)$ and the method does not entirely eliminate the effects of varying background temperatures. In the design of the GFC in this invention, the previous method is improved upon by measuring $\epsilon E(T_S)$ in the 10 micron "window," $T_A$ with a thermometer, and the atmospheric relative humidity with a psychrometer, and then using a microprocessor to compute $[\epsilon E(T_S) - E(T_A)]\tau_W$ in the 3000–3030 cm$^{-1}$ band. This factor is continuously ratioed with the measured SC. The GFC output (FIG. 3) displays this ratio which is independent of target and atmospheric temperature variations. It is noted that $\epsilon E(T_S)$ resulting from solar radiation cannot be measured in the 4 micron "window". In addition, it is advantageous to use the 10 micron "window" since the emissivities of most surfaces are quite similar at 3.3 microns and 10 microns, but not at 3.3 microns and 4 microns.

To partially re-state the foregoing paragraph so as to assure clarity, the surface temperature uniquely determines the blackbody radiance at all wavelengths. Thus measuring the radiance at 10 microns permits calculating the radiance at 3.3 microns, provided the values of emissivity are similar, which is true for most terrains at those two specific wavelengths. Similarly, measuring the atmospheric temperature permits calculating the value of $E(T_A)$ at 3.3 microns. The radiances are calculated from the Planck Blackbody Function. Because the computations are lengthy they can best be calculated either with a microprocessor or a range of values stored in a read-only memory (ROM) and accessed directly by the measured data as a lookup table.

Figure 2:
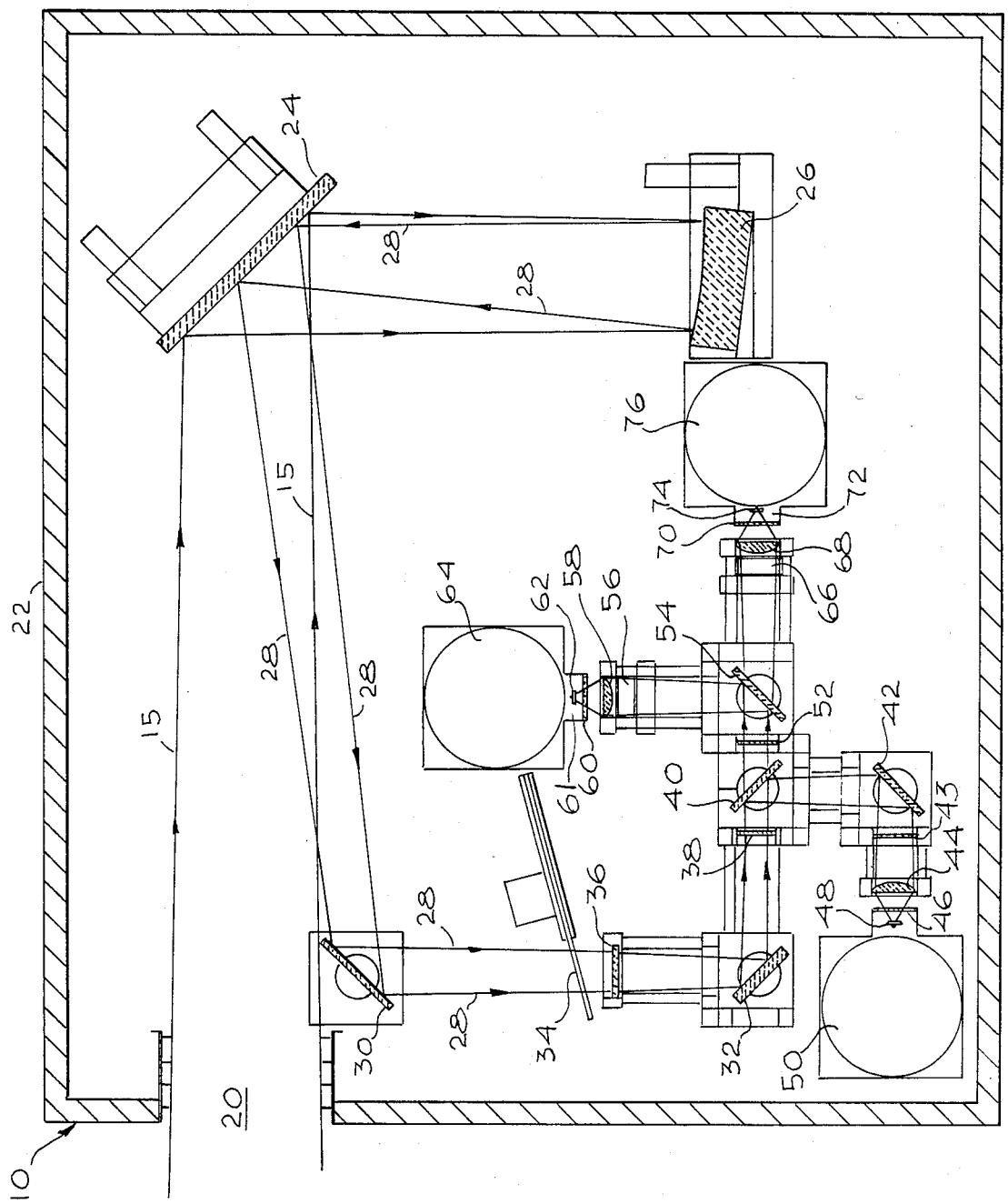
FIG. 2 is a schematic mechanical diagram of a portion of the present invention; and, FIG. 3 is a block diagram of apparatus according to the present invention.

The optical details of th RGFC methane sensor are shown in FIG. 2. In FIG. 2, infrared radiation 15 from a surface, not shown, enters sensor 10 through a port 20 in housing 22 and strikes 45° mirror 24 which cooperates with mirror 26 to form a portion of a folded telescope, thus reducing the size of sensor 10 without reducing the focal length of its optics. Mirror 26 is tilted, as shown, to produce a tilted return beam 28 which again strikes mirror 24 and is reflected onto the sloping surface of diagonal mirror 30. Beam 28 is then directed by mirror 30 to folding mirror 32 by way of chopping blade 34 and field lens 36. The beam 28 as reflected off folding mirror 32 passes through relay lens 38 onto beam splitter 40 which selectively transmits 3.3 micron energy and reflects 10 micron energy. The 10 micron energy thus is directed to folding mirror 42 and, thence, through 10 micron bandpass filter 43, detector lens 44 and dewar window 46 onto HgCdTe detector 48, which is photoconductive. Dewar 50 has x, y and z axes translation stages and maintains detector 48 at 77° Kelvin, to maximize detection efficiency and signal-to-noise ratio.

The 3.3 micron energy passing through selective beam splitter 40 encounters narrow bandpass filter 52 before falling upon the surface of second beam splitter 54. There the beam is split in two, half being transmitted and half being reflected. The half which is reflected passes through vacuum gas cell 56, second detector lens 58, second dewar window 60 and cold filter 61 before falling on Indium Antimonide InSb photovoltaic detector 62. Detector 62 is maintained at 77° Kelvin in dewar 64. Dewars 50 and 64 utilize liquid nitrogen to maintain these cryogenic conditions.

The 3.3 micron energy passing through beam splitter 54 traverses methane gas cell 66, detector lens 68, dewar window 70 and cold filter 72 before falling on InSb photovoltaic detector 74. Liquid nitrogen in dewar 76 maintains detector 74 at 77° Kelvin. Dewar 76 is also capable of x, y and z axis translation for alignment purposes.

It may be seen from FIG. 2 that the optical channel to observed-surface-temperature sensor 48, operating at 10 microns, is optically aligned with the two 3.3 micron channels which terminate in sensors 62 and 74, respectively. Thus, all three channels are "seeing" (or receiving their radiant energy from) the same observed area, and correlation of the signal levels out of the three sensors, 48, 62 and 74 is simplified.

Figure 3:
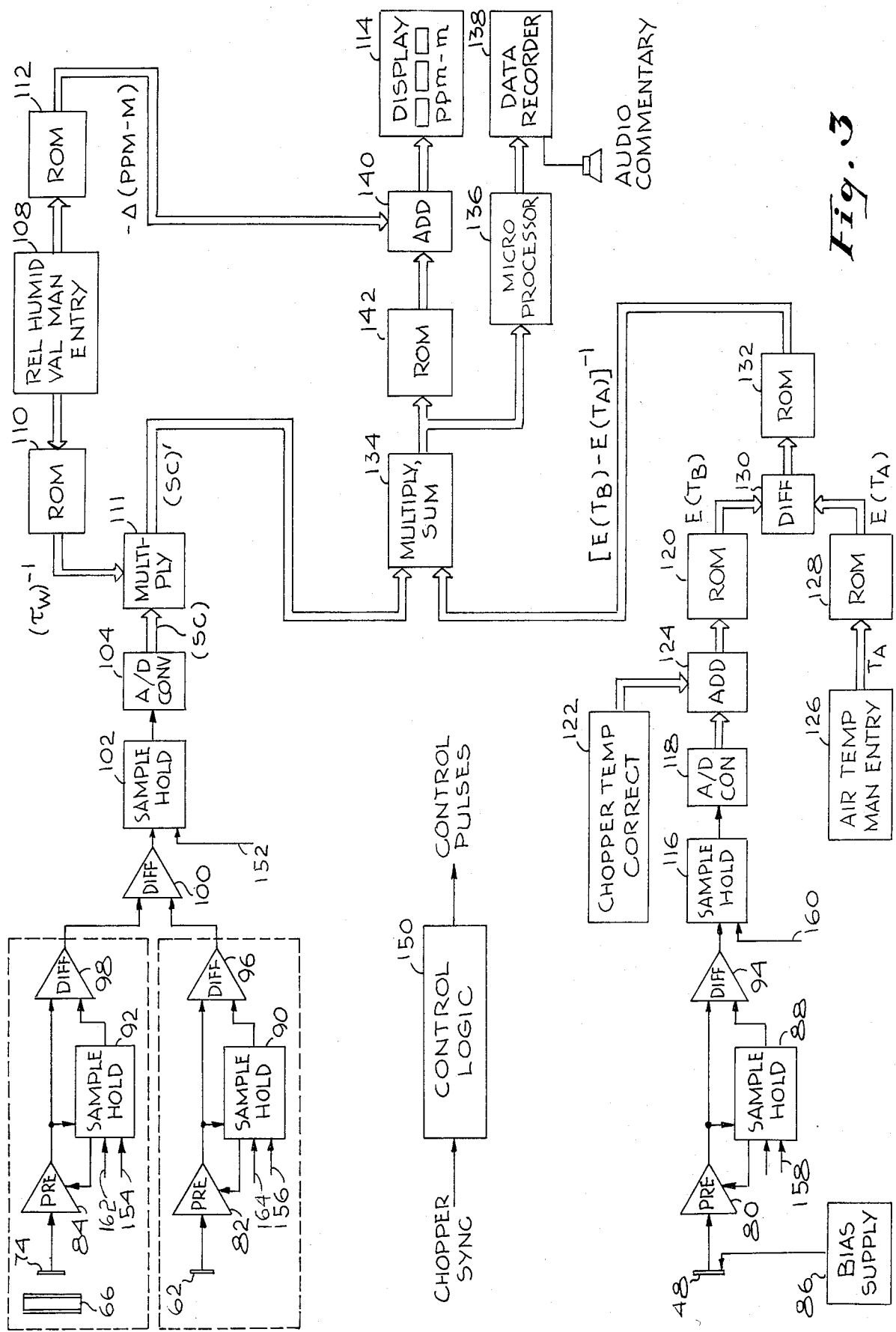

The processing of the data from sensors 48, 62 and 74 to give a measure of methane gas concentration at a remote point is performed in digital, real-time fashion in the circuit of FIG. 3.

The output signals from detectors 48, 62 and 74 are fed to pre-amps 80, 82 and 84, respectively. Because of the photoconductive nature of detector 80 it requires a biasing voltage, which is derived from supply 86.

Detectors 62 and 74 are in the GFC signal channel and detector 48 provides a radiometric correction signal for use in connection with the GFC signal.

The output of each of the pre-amps 80, 82 and 84 is a d.c. coupled signal. Each output contains a d.c. component, which is a function of the temperature of its associated detector, and a periodic component at the frequency of chopper blade 34. These components are separated from each other by using sample/hold circuits 88, 90 and 92 and differential amplifiers 94, 96 and 98, respectively.

For each of the three detectors, 48, 62 and 74, the signals will be sampled simultaneously at the time when the detectors are viewing the reference surface of the chopper balde 34. This value is a function of the temperature of the reference surface of the blade and the responsivity of the detector, which depends on the detector temperature. This reference surface measurement is used for two purposes.

First, it is used, if required, for detector-temperature gain correction. The detectors 48, 62 and 74 are designed to operate at 77 degrees Kelvin and are mounted in $LN_2$ dewars 50, 64 and 76 having a nominal 12-hour operating time between refills. If a detector is at 77 degrees Kelvin, its output when viewing the chopper reference surface can be predicted and compared with the measured value. They are expected to agree. If they do not agree, a temperature error exists at the detector and a feedback loop (not shown) within each pre-amp adjusts the gain of the pre-amp so that the GFC or radiometric signal will not be affected by any such temperature error.

Second, this reference-surface measurement is the reference from which the radiant input from the target field of view is measured. This is accomplished by taking the instantaneous difference between the sampled reference level for each detector and the subsequent signal when the chopper opens and exposes the detectors, 48, 62 and 74, to the target.

The outputs of differential amplifiers 98, 96 and 94 are (1) the 3.3 micron differential GFC signal taken through the methane cell 66, (2) the 3.3 micron GFC signal bypassing the methane cell 66, and (3) the 10 micron radiometric signal.

The two 3.3 micron signals are differenced in the following differential amplifier 100 to generate the (SC) signal. This signal must be corrected for ground and atmospheric radiance before the data output can be examined. This radiance correction must take place at a rate which is as fast as significant changes are expected to occur due, for example, to flight velocity over the test terrain. This correction should be made at intervals of no longer than 0.1 msec (the target is viewed for 10 msec periods at a chopping frequency of 100 Hz). This data is sampled in sample/hold circuit 102, digitized at this rate in A/D converter 104 and corrected for radiance in the multiply/sum unit 134. Prior to this correction, the (SC) signal is corrected for $\tau_W$ [see Equation (5)] by manually entering the relative humidity in a ROM look-up table 108 which will read out the corresponding $(\tau_W)^{-1}$ value from ROM 110. This value is multiplied with (SC) in multiplier 111 to provide (SC), which is subsequently corrected for radiance. This same relative humidity entry develops a signal from ROM 112 to correct the measured methane thickness for water vapor interference immediately before display on display 114.

The radiometric (E) signal is sampled in sample/hold 116 and digitized by A/D converter 118 simultaneously with the digitizing of (SC) signal. The "E" signal at this point is proportional to the difference in radiance, measured at 10 microns, between the reference surface of chopper blade 34 and that of the outside terrain. This must be changed into the value of the surface terrain radiance at 3.3 microns. This conversion will be accomplished in read-only-memory (ROM) 120 in which is stored the 3.3 micron surface radiance corresponding to values of 10 micron terrain-minus-chopper radiance. An additive correction is available from chopper temp. correct element 122 thru adder 124 to adjust the input signal "E" if the chopper reference surface temperature is different from that assumed in the calculation of values for the ROM 120 look-up table.

The correction applied to the (SC) signal is the difference in radiance at 3.3 micron between the terrain and atmosphere. The atmospheric temperature is monitored and entered manually thru air temp manual entry 126 to a second ROM lool-up table 128 which reads out the equivalent 3.3 micron radiance. The terrain and atmospheric radiances are digitally subtracted in difference element 130 to obtain the corrective term.

The desired signal is the ratio between the (SC) and the radiance term. This division can be implemented in software with a microprocessor but the resulting calculation is time consuming. A more efficient method is to use a third ROM 132 to provide the inverse of the radiance term, and an integrated circuit multiplier/summer 134 to obtain the desired ratio. The rapid sequence of data values is summed in element 134 over each chopper cycle and becomes the output to the display 114 and to the storage system including microprocessor 136 and data recorder 138.

The digital data may be stored on a standard audio cassette recorder 138. Microprocessor 136 provides the interface/format functions so that the data is stored in a standard format for later retrieval and analysis. By using a stereo recorder at 138, a second channel is available for simultaneous audio commentary by a flight observer.

The digital data from multiplier-summer 134 may also be converted to equivalent ppm-m ($=10^4$ atm-cm) by means of the look-up table including relative humidity manual entry element 108 and ROM 112, the corrective term being added at adder 140 following ROM 142, and visually displayed on a digital or analog readout 114 for the flight observer.

It is possible to incorporate a small television camera and video tape recorder in the system so that the actual instantaneous ground scene is recorded with its related data and voice commentary.

Timing pulses for controlling the system are derived from control logic 150 in response to synchronizing pulses by or in connection with chopper blade 34. Such timing pulses are supplied, for example, to sample-command input terminal 152, 154, 156, 158 and 160 of sample/hold circuits 102, 92, 90, 88 and 116, respectively. Reference voltages may be applied to reference terminals 162, 164 and 166 of sample/hold circuits 92, 90 and 88, respectively.

While a particular enbodiment of this invention has been shown and described, it will be apparent to one ordinarily skilled in the art that modifications and variations may be made in the disclosed embodiment without departing from the spirit and scope of this invention. It is the purpose of the appended claims to cover all such modifications and variations.

What is claimed is:

1. Apparatus for accurate remote monitoring of the concentration of a target gas, which includes;
    first and second gas filter correlation channels both operating at a first spectral wavelength and each having an output terminal;
    differential amplifier means having first and second input terminals coupled to respective ones of said output terminals of said first and second gas filter correlation channels for producing a first output signal which represents the target gas but requires correction for ambient conditions;
    a corrective channel operating at a second spectral wavelength substantially different from said first spectral wavelength for producing a second output signal representative of said ambient conditions;
    signal multiplying means coupled to said differential amplifier means and to said corrective channel for multiplying said first and second output signals to produce a target-gas concentration signal, said pair of gas filter correlation channels and said corrective channel being optically aligned to receive radiant energy from a common source region; and,
    means to utilize said gas concentration signal.

2. Apparatus according to claim 1 in which said corrective channel includes radiance difference means for generating a radiance signal representative of the difference between terrain and atmospheric radiances and means coupled to said radiance difference means for inverting said radiance signal to produce said second output signal.

3. Apparatus according to claim 1 in which said pair of gas filter correlation channels includes a common narrow-bandpass optical filter centered at said first spectral wavelength.

4. Apparatus according to claim 3 in which said target gas is methane and said narrow-bandpass optical filter is centered at 3.3 microns.

5. Apparatus according to claim 3 in which said second spectral wavelength is 10 microns.

6. Apparatus according to claim 1 in which said pair of gas filter correlation channels includes photovoltaic energy sensors and said corrective channel incudes a photoconductive energy sensor.

7. Apparatus according to claim 6 in which said photovoltaic sensors are of InSb and said photoconductive sensor is of HgCdTe.

8. Apparatus according to claim 1 which includes, in addition, means for correcting said first output signal for the effects of relative atmospheric humidity.

9. The method of accurately and remotely measuring, for a region being observed, the concentration of a target gas having, under natural conditions, a high absorption at a predetermined first spectral wavelength, which includes the steps of:
    collecting radiant energy from said region to be observed;
    chopping said radiant energy in a cylical manner to produce cylically chopped radiant energy;
    splitting said chopped radiant energy into first and second beams of chopped radiant energy, one at said first spectral wavelength and the other at a second spectral wavelength significantly different from said first spectral wavelength;
    passing said first beam of chopped radiant energy thru a narrow-bandpass filter centered at first wavelength;
    processing said first beam, after it passes thru said narrow-bandpass filter, in a pair of gas filter correlation channels to produce a first processing signal and a second processing signal, respectively;
    differentially amplifying said first processing signal and said second processing signal to produce a first output signal representative of all energy received from said region to be observed at said first spectral wavelength;
    processing said second beam in a third channel to produce a second output signal which is representative of the difference between background radiant energy and atmospheric radiant energy at said second spectral wavelength;
    multiplying said first output signal by said second output signal, at any instant, to produce an instantaneous target-gas concentration signal; and,
    summing said instantaneous target gas signals over a chopping cycle.

10. The method according to claim 9 in which the target gas is methane, the first spectral wavelength is 3.3 microns and the second spectral wavelength is 10 microns.

11. The method according to claim 9 which includes the additional step of correcting said first output signal for percentage of relative humidity in the atmosphere being observed.

12. The method according to claim 9 which includes the additional step of displaying the results of said summation.

13. The method according to claim 9 including, in addition, the step of recording the results of the summing.

14. The method according to claim 9 in which said processing of said second beam includes the step of correcting for the temperature of the surface involved in said cyclical chopping.

* * * * *